United States Patent
Kim et al.

(10) Patent No.: US 6,822,735 B2
(45) Date of Patent: Nov. 23, 2004

(54) MICRO-BUBBLE ANALYZING APPARATUS FOR HIGH-PURITY GLASS TUBE USING LASER LIGHT SCATTERING

(75) Inventors: Byoung-Sam Kim, Kumi-shi (KR); Young-Min Baik, Kumi-shi (KR); Mi-Kyung Lee, Kumi-shi (KR); Hyung-Min Lee, Kumi-shi (KR)

(73) Assignee: Samsung Electronics Co., Ltd., Suwon-si (KR)

(*) Notice: Subject to any disclaimer, the term of this patent is extended or adjusted under 35 U.S.C. 154(b) by 0 days.

(21) Appl. No.: 10/298,982

(22) Filed: Nov. 18, 2002

(65) Prior Publication Data

US 2003/0107730 A1 Jun. 12, 2003

(30) Foreign Application Priority Data

Dec. 6, 2001 (KR) .................................. 2001-76818

(51) Int. Cl.[7] .............................................. G01N 21/00
(52) U.S. Cl. .............................. 356/239.1; 356/239.4; 356/239.5; 250/223 B; 250/559.45; 209/524
(58) Field of Search ........................... 356/239.1–239.8, 356/237.1, 238.1, 238.3, 240.1; 250/223 B, 224, 559.45, 338.1, 561, 562, 559.48; 209/524

(56) References Cited

U.S. PATENT DOCUMENTS

| | | | | |
|---|---|---|---|---|
| 4,168,907 A | | 9/1979 | Presby | 356/73.1 |
| 4,171,481 A | * | 10/1979 | Mima et al. | 250/223 B |
| 4,363,966 A | * | 12/1982 | Cheo | 250/338.1 |
| 4,376,951 A | * | 3/1983 | Miyazawa | 348/127 |
| 4,492,476 A | * | 1/1985 | Miyazawa | 356/428 |
| 4,500,203 A | * | 2/1985 | Bieringer | 356/239.4 |
| 4,679,075 A | * | 7/1987 | Williams et al. | 348/127 |
| 4,736,851 A | * | 4/1988 | Ricros et al. | 209/524 |
| 5,136,157 A | * | 8/1992 | Apter et al. | 250/223 B |
| 5,249,034 A | * | 9/1993 | Minato | 356/606 |
| 5,406,374 A | | 4/1995 | Shimada et al. | 356/73.1 |
| 5,459,330 A | * | 10/1995 | Venaille et al. | 250/559.45 |
| 5,729,340 A | * | 3/1998 | Griesbeck et al. | 356/240.1 |
| 6,294,793 B1 | * | 9/2001 | Brunfeld et al. | 250/559.45 |
| 6,356,346 B1 | * | 3/2002 | Hagen et al. | 356/237.1 |
| 6,369,889 B1 | * | 4/2002 | Olschewski | 356/239.4 |
| 6,424,414 B1 | * | 7/2002 | Weiland et al. | 356/239.4 |

FOREIGN PATENT DOCUMENTS

| | | | | |
|---|---|---|---|---|
| JP | 08-166356 | | 6/1996 | G01N/21/89 |
| JP | 08254505 A | * | 10/1996 | G01N/21/90 |
| JP | 09-292305 | | 11/1997 | G01M/11/00 |
| JP | 11-64231 | | 5/1999 | G01N/21/88 |
| JP | 11 258167 | * | 9/1999 | |

* cited by examiner

Primary Examiner—Gregory J. Toatley, Jr.
Assistant Examiner—Sang H. Nguyen
(74) Attorney, Agent, or Firm—Cha & Reiter, L.L.C.

(57) ABSTRACT

Enclosed is an apparatus for analyzing micro-bubbles inside a high-purity glass tube by using a laser light dispersion. The apparatus includes: an optical base having a sample stage in a substantially horizontal orientation; a glass tube rotably mounted on the optical base in a substantially vertical orientation, the glass tube being rotated and translated in a vertical direction at a predetermined speed via the sample stage; a light generator disposed at one side of the glass tube for selectively irradiating a laser light onto an outer surface of the glass tube at a prefixed angle; and, a detector disposed at the other side of the glass tube for detecting the distribution and amount of micro-bubbles of the glass tube using the laser light passed through the glass tube.

11 Claims, 2 Drawing Sheets

MICRO-BUBBLE ANALYZING APPARATUS FOR HIGH-PURITY GLASS TUBE USING LASER LIGHT SCATTERING

CLAIM OF PRIORITY

This application makes reference to and claims all benefits accruing under 35 U.S.C. Section 119 from an application entitled, "MICRO-BUBBLE ANALYZING APPARATUS FOR HIGH-PURITY GLASS TUBE USING LASER LIGHT SCATTERING," filed in the Korean Industrial Property Office on Dec. 6, 2001 and there duly assigned Serial No. 2001-0076818.

BACKGROUND OF THE INVENTION

1. Field of the Invention

The present invention generally relates to high-purity overcladding glass tubes fabricated by a sol-gel process. More particularly, the present invention relates to an apparatus that is capable of analyzing micro-bubbles of the high-purity overcladding glass tubes three-dimensionally.

2. Description of the Related Art

In general, optical-fiber parent metals are fabricated by vapor deposition and liquid deposition techniques. The most widely used vapor deposition method includes a chemical vapor deposition (CVD) or a modified chemical vapor deposition (MCVD) process, and the sol-gel process is a common liquid deposition. Recently, because of economical efficiency and facility in fabrication, the sol-gel process has been favored over other processes for fabricating large diameter optical-fiber parent metals. The optical-fiber parent metals aforementioned include rod-shaped primary optical-fiber parent metals and tube-type secondary optical-fiber parent metals (over-cladding glass tubes). During the manufacturing stage, it is important to analyze the characteristics of the glass tubes, such as a micro-bubble formed inside the glass tubes.

FIG. 1 is a schematic diagram illustrating a micro-bubble analyzing apparatus for an overcladding glass tube 12 in accordance with one embodiment of a related art. The glass tube 12 shown in FIG. 1 is fabricated by a sol-gel process for use in fabricating the large diameter optical-fiber parent metal using the sol-gel process. Briefly, to fabricate the overcladding glass tube 12, a colloidal sol is first manufactured and injected into a mold to produce a gel to a desired shape. Then, following the consecutive processes of drying, removing organic materials, low-heat treatment and sintering, the glass tube is ultimately fabricated.

However, the high-purity silica glass tube is often degraded due to bubbles and organic byproducts that are sometimes produced during the injection process of the colloidal sol into the mold, whereas micro-bubbles form because the sintering process is not precisely performed. To overcome the problem, a micro-bubble analyzing apparatus depicted in FIG. 1 has been introduced.

As depicted in the drawing, the analyzing apparatus in the related art comprises the glass tube 12 prepared by the sol-gel process at the center, a laser 10 at one side and a screen 14 at the other side. In the FIG. 1, the drawing reference numeral 10a indicates the laser light irradiated to the glass tube, and the 10b indicates a transmitted light after the laser light transmits the glass tube 12. If the laser 10 is vertically irradiated to the outer surface of the glass tube 12, the laser light passes through the glass tube 12 into the interior of the tube and is reflected as an image on the screen placed at the rear surface of the glass tube 12. By analyzing the image on the screen 14, it is possible to evaluate the micro-bubbles remaining inside the glass tube 12.

Still there exists another problem when the laser is vertically irradiated onto the glass tube for the analysis of the transmitted light. That is, it is observed that the light is often distorted as the laser light is reflected, refracted, and dispersed according to the surface state and shape of the cylindrical glass tube. As such, only a rough analysis on the distribution of the micro-bubbles in the glass tube and damages thereon is possible, and a more precise analysis on the micro-bubbles and the damages is not feasible in the current state of art. In addition, the conventional analyzing apparatus is not capable of analyzing the three-dimensional position, size and content level of the micro-bubbles in the glass tube.

SUMMARY OF THE INVENTION

The present invention is related to a micro-bubble analyzing apparatus which enables a precise analysis of the conditions of the micro-bubbles of a glass tube.

One aspect of the present invention is to provide a micro-bubble analyzing apparatus that enables the fabrication of high-reliability/high-purity glass tubes.

Accordingly, there is an apparatus for analyzing a micro-bubble inside a glass tube for use in optical-fiber basic materials, which includes: (a) an optical base having a sample stage in a substantially horizontal orientation; (b) a glass tube rotably mounted on the optical base in a substantially vertical orientation, the glass tube being rotated and translated in a vertical direction at a predetermined speed via the sample stage; (c) a light generator disposed at one side of the glass tube for selectively irradiating a laser light onto an outer surface of the glass tube at a prefixed angle; and, (d) a detector disposed at the other side of the glass tube for detecting the distribution and amount of micro-bubbles of the glass tube using the laser light passed through the glass tube.

BRIEF DESCRIPTION OF THE DRAWINGS

The above features and advantages of the present invention will become more apparent from the following detailed description when taken in conjunction with the accompanying drawings in which.

DETAILED DESCRIPTION OF THE PREFERRED EMBODIMENT

In the following description, for purposes of explanation rather than limitation, specific details are set forth such as the particular architecture, interfaces, techniques, etc., in order to provide a thorough understanding of the present invention. For the purpose of clarity and simplicity, well-known functions or constructions are not described in detail as they would obscure the invention in unnecessary detail.

Figure 1:
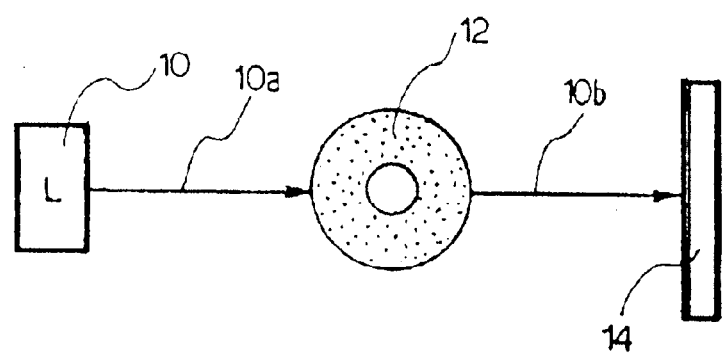
FIG. 1 is a schematic diagram illustrating a bubble-analyzing apparatus in accordance with one embodiment of a related art.
Figure 2:
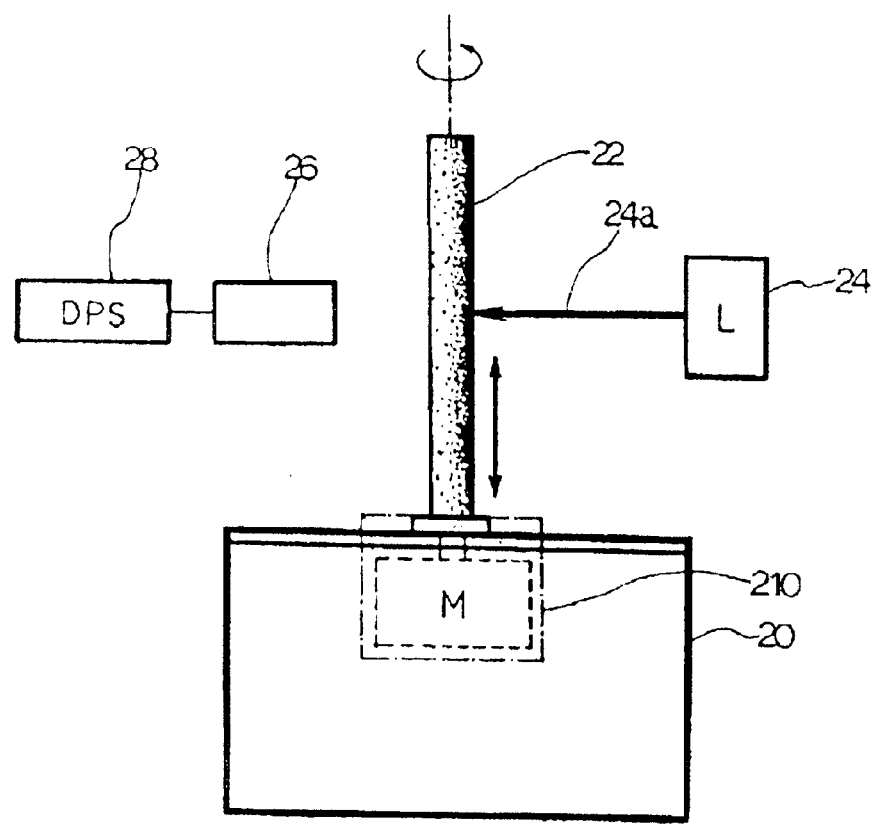
FIG. 2 is a schematic diagram illustrating a micro-bubble analyzing apparatus in accordance with a preferred embodiment of the present invention.
Figure 3:
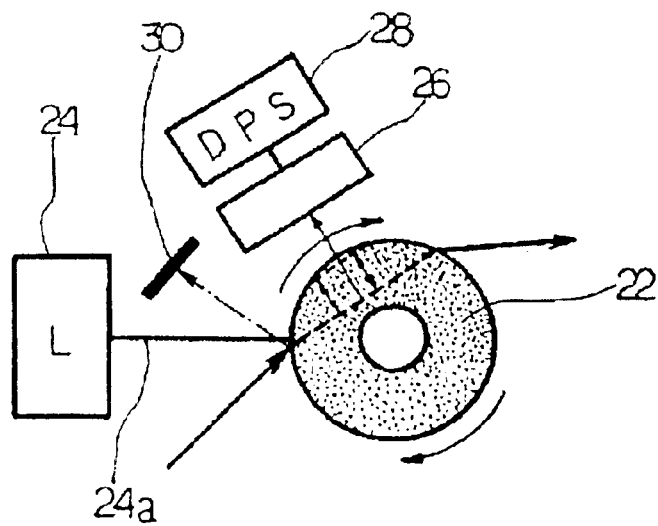
FIG. 3 is a diagram illustrating an array of the analyzing apparatus depicted in FIG. 2; and, FIG. 4 is a diagram illustrating an array of a bubble-analyzing apparatus in accordance with another preferred embodiment of the present invention.

FIGS. 2 and 3 represent a simplified block diagram of an optical-fiber analyzing arrangement, including a hallow glass tube 22, whereto the embodiment of the present invention may be applicable.

As shown in FIG. 2 and FIG. 3, the high-purity glass tube 22 indicates a primary optical-fiber parent metal and a secondary optical-fiber parent metal, respectively, which are manufactured to fabricate a large diameter optical-fiber parent metal. More specifically, the primary optical-fiber parent metal is a rod-shaped glass tube, and the secondary optical-fiber parent metal is a hollow glass tube. The primary optical-fiber parent metal with a rod shape and the secondary optical-fiber parent metal in a hollow shape are overcladded to fabricate the large diameter optical-fiber parent metals.

The analyzing apparatus according to the present invention comprises an optical base 20 having a sample stage 210 in a substantially horizontal orientation, a glass tube 22 rotably mounted on the optical base 20 in a substantially vertical orientation, the glass tube 22 being rotated and translated in a vertical direction at a predetermined speed via the sample stage 210, a light generator 24 disposed at one side of the glass tube, and, either a CCD detector 26 or PMT (PhotoMultiplier Tube) detector 26 disposed at the other side of the glass tube 22.

The sample stage 210 with a motor (not shown) is disposed at the central part of the optical base and provides a hole thereto through which the glass tube is rotably mounted in a substantially horizontal direction. The glass tube 22 rotates and translates in a vertical direction via the sample stage 210, so it is possible to make a three-dimensional analysis on the glass tube 22.

If a CCD detector is used, the CCD detector 26 photographs pass lines of the dispersed light by the micro-bubbles and separates the light into three colors (red/green/blue). Then, the CCD detector 26 analyzes the position and size of the micro-bubbles at a small part inside the glass tube based on the intensity of the dispersed light.

If a PMT detector is used, the PMP detector 26 measures the intensity of the dispersed light based on the pass lines of the dispersed light by the micro-bubbles inside the glass tube 22 when a He—Ne laser is irradiated onto the glass tube 22. Also, a lens for passing through a light in a He—Ne wavelength region can be installed only at the front end of the PMT detector 26 to measure only the intensity of the dispersed light by the micro-bubbles inside the glass.

The apparatus of the present invention also includes an image detector 26 for detecting the surface of the glass based on the analysis on the light reflected by the surface of the glass tube 22.

When the sample stage 210 operates, the glass tube 22 connected to the sample state 210 rotates and translates in a vertical direction at the same speed to the same direction with the sample stage. Then, a laser light 24a from the laser or the light generator 24 is irradiated to the entire surface of the glass tube at regular intervals. More specifically, the laser light 24a is irradiated onto an outer surface of the glass tube at a prefixed angle. Once the laser light 24a passes through the glass tube 22, the detector 26 detects the dispersion intensity of the transmitted light 24b from the glass tube 22. Of course, the remaining micro-bubbles in the glass tube 22 disperse the light.

Preferably, a He—Ne laser is used as the light generator 24. After irradiating the light generator onto the glass tube 22, the transmitted light 24b from the glass tube 22 can analyze the micro-bubbles inside the glass tube three-dimensionally by using the CCD detector 26 or PMT detector 26. Signals detected by the detector 26 are then provided to a data-processing system 28 and processed therein. Moreover, the surface of the glass tube can be analyzed by analyzing the light reflected by the surface of the glass using the image detector.

If the CCD detector 26 is used for detecting the transmitted light 24b, it photographs laser pass lines going through the inside of the glass tube 22 from a vertical direction, and detects electric signals out of the intensity of the dispersed light by the micro-bubbles at a position where light passes. The electric signals of the dispersed light are sent to the data-processing system 28. On the other hand, if the PMT detector 26 is used as the detector of the transmitted light 24b, a lens is mounted on the front end of the PMT detector 26 for analyzing the dispersed light by the micro-bubbles inside the glass and disregarding light in other regions rather than the He—Ne laser region. After detecting the dispersed light, electric signals therefrom are sent to the data-processing system 28.

FIG. 3 represents laser pass lines when the light generator 24 irradiates the laser light 24a onto the glass tube 22. Actually, the laser pass lines are the dispersed light by the micro-bubbles inside the glass tube 22. The degree of dispersion is different depending on the amount and the distribution of the bubbles. A quantitative analysis of the dispersed light can be made by the CCD detector 26 based on the electric signal analysis.

Instead of the CCD detector, the PMT detector can be used to find out the distribution state of the micro-bubbles by measuring perpendicularly dispersed light caused by specific micro-bubbles regardless of the reflection by the surface of the glass tube. As mentioned before, either the CCD detector or the PMT detector can be used as the detector 26. In addition, the glass image detector 30 can analyze the surface of the glass tube by analyzing the light reflected by the surface.

Figure 4:
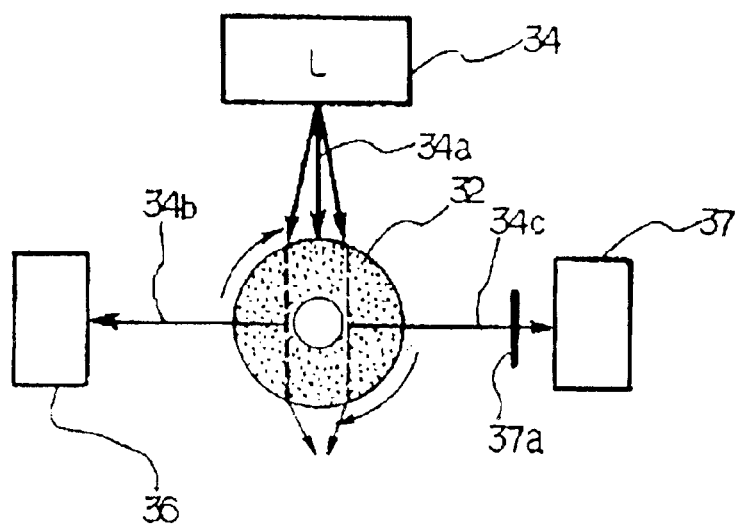

As depicted in FIG. 4, the analyzing apparatus according to another embodiment of the present invention includes a CCD detector 36 or the PMT detector 37 disposed at a certain distance from the glass tube, facing the glass tube 32 at the center. The glass tube 32 rotates by a motor (not shown) at a prefixed speed, and the laser light 34a from the laser 34 is irradiated onto the outer surface of the glass tube 32 at a prefixed angle.

The CCD detector 36 or the PMT detector 38 detects the micro-bubble content in the glass tube 32 by analyzing the transmitted lights 34a and 34b that had passed through the glass tube 32. Moreover, the micro-bubble content can be found by adjusting the irradiation angle of light emitted from the laser 34 and selecting an appropriate detector for such cases. Additionally, if the He—Ne laser is used as the light generator, a lens 37a for passing light within the He—Ne wavelength region only is added onto the front end of the PMT detector 37 to measure exclusively the intensity of the dispersed light by the micro-bubbles inside the glass tube.

As is apparent from the foregoing, the analyzing apparatus of the present invention enables the detection of micro-bubbles inside the glass tube 22 that rotates according to the electric signals by employing the CCD detector or PMT detector, and to find out the three-dimensional distribution state of the micro-bubbles based on the electric signals provided to the data-processing system 28 from each detector.

Accordingly, the present invention is very advantageous to a systematic and three-dimensional analysis of the micro-bubbles remaining inside the high-purity silica glass tube, which eventually enables the fabrication of optical-fiber parent metals with high-reliability.

While the preferred embodiments of the present invention have been illustrated and described, it will be understood by those skilled in the art that various changes and modifications may be made, and equivalents may be substituted for elements thereof without departing from the true scope of the present invention. In addition, many modifications may be made to adapt to a particular situation and the teaching of the present invention without departing from the central scope. Therefore, it is intended that the present invention not be limited to the particular embodiment disclosed as the best mode contemplated for carrying out the present invention, but that the present invention include all embodiments falling within the scope of the appended claims.

What is claimed is:

1. An apparatus for analyzing micro-bubbles inside a glass tube, comprising:
    (a) an optical base having a sample stage in a substantially horizontal orientation;
    (b) a glass tube rotatably mounted on the optical base in a substantially vertical orientation, the glass tube being rotated and translated in a vertical direction at a predetermined speed via the sample stage;
    (c) a light generator disposed laterally to face the glass tube for selectively irradiating a laser light onto an outer surface of the glass tube at a prefixed angle; and,
    (d) a detector disposed laterally to face the glass tube for detecting distribution and amount of micro-bubbles in the glass tube using the laser light passed through the glass tube.

2. The apparatus as claimed in claim 1, wherein the light generator is a helium-neon laser.

3. The apparatus as claimed in claim 1, wherein the detector is a charge coupled device (CCD) detector.

4. The apparatus as claimed in claim 1, wherein the detector is a photo-multiplier tube (PMT) detector.

5. The apparatus as claimed in claim 4, wherein the detector further includes a lens at the front end of the detector for transmitting light at a specific wavelength region.

6. The apparatus as claimed in claim 1, wherein the detector detects perpendicularly dispersed light caused by the micro-bubbles of the glass tube.

7. The apparatus as claimed in claim 1, further comprising an image detector disposed adjacent to the glass tube for analyzing light reflected by the surface of the glass tube.

8. An apparatus for analyzing micro-bubbles inside a glass tube, comprising:
    (a) an optical base having a sample stage;
    (b) a glass tube rotatably mounted on the optical base in a substantially vertical direction, the glass tube being rotated at a predetermined speed via the sample stage;
    (c) a laser source disposed at one side of the glass tube for irradiating a laser light at a prefixed angle onto an outer surface of the glass tube;
    (d) a charge coupled device (CCD) detector disposed laterally to face the glass tube and disposed perpendicular to the laser source, for detecting micro-bubbles of the glass tube based on dispersed light responsive to the irradiated laser light passed through the glass tube; and,
    (e) a photo multiplier tube (PMT) detector disposed laterally to face the glass tube and disposed opposite the CCD detector, for detecting the intensity of the dispersed light.

9. The apparatus as claimed in claim 8, further comprising an image detector disposed adjacent to the glass tube for analyzing light reflected by the surface of the glass tube.

10. The apparatus as claimed in claim 8, further comprising a motor coupled to the optical base for rotating the glass tube.

11. The apparatus as claimed in claim 8, wherein the glass tube is translated in a vertical direction at a predetermined speed.

* * * * *